United States Patent [19]

Graves et al.

[11] Patent Number: 5,496,274
[45] Date of Patent: Mar. 5, 1996

[54] LOCKING SAFETY NEEDLE ASSEMBLY

[75] Inventors: Arlinda Graves, Stamford, Conn.; Niall Sweeney, Rutherford; Sandor Szabo, Elmwood Park, both of N.J.

[73] Assignee: Becton, Dickinson and Company, Franklin Lakes, N.J.

[21] Appl. No.: 297,347

[22] Filed: Aug. 29, 1994

Related U.S. Application Data

[63] Continuation-in-part of Ser. No. 979,959, Nov. 23, 1992, abandoned.

[51] Int. Cl.$^6$ .......................... A61M 37/00; A61M 5/32; A61M 5/00
[52] U.S. Cl. ............... 604/86; 604/192; 604/263
[58] Field of Search ..................... 604/192, 198, 604/263, 83, 86, 87, 88, 280, 283, 905

[56] References Cited

U.S. PATENT DOCUMENTS

| | | | |
|---|---|---|---|
| Re. 33,617 | 6/1991 | Ogle, II | 604/192 |
| 4,123,091 | 10/1978 | Cosentino et al. | 285/39 |
| 4,790,829 | 12/1988 | Bowden et al. | 604/244 |
| 4,792,163 | 12/1988 | Kulle | 285/88 |
| 4,826,486 | 5/1989 | Palsrok et al. | 604/174 |
| 4,838,871 | 6/1989 | Luther | 604/192 |
| 4,946,445 | 8/1990 | Lynn | 604/192 |
| 4,950,260 | 8/1990 | Bonaldo | 604/283 |
| 4,966,588 | 10/1990 | Rayman et al. | 604/165 |
| 4,981,469 | 1/1991 | Whitehouse et al. | 604/86 |
| 5,135,509 | 8/1992 | Oliffe | 604/192 |
| 5,137,524 | 8/1992 | Lynn et al. | 604/283 |
| 5,139,483 | 8/1992 | Ryan | 604/86 |
| 5,199,947 | 4/1993 | Lopez et al. | 604/56 |
| 5,199,948 | 4/1993 | McPhee | 604/86 |
| 5,207,667 | 5/1993 | Walker et al. | 604/905 |
| 5,248,306 | 9/1993 | Clark et al. | 604/283 |
| 5,281,206 | 1/1994 | Lopez | 604/283 |
| 5,282,794 | 2/1994 | Propp | 604/283 |
| 5,290,222 | 3/1994 | Feng et al. | 604/86 |
| 5,356,396 | 10/1994 | Wyatt et al. | 604/283 |

FOREIGN PATENT DOCUMENTS

WO90/05559  5/1990  WIPO .

*Primary Examiner*—John D. Yasko
*Assistant Examiner*—Adam J. Cermak
*Attorney, Agent, or Firm*—J. L. Voellmicke; V. A. Castiglione

[57] ABSTRACT

A safety needle assembly for providing secure connection of a needle cannula to a straight-site or Y-site of an intravenous fitting. The assembly includes a base portion and a protective shield disposed about the needle cannula to at least partially envelop the needle cannula within the shield. A latch is pivoted to the shield so as to releasably lock the intravenous fitting within the shield. The latch includes a pivot arm having at least one shield engaging finger member disposed to biasingly engage at least a portion of the shield, and at least one member disposed through a passageway formed in the shield to trap the intravenous fitting within the shield.

31 Claims, 7 Drawing Sheets

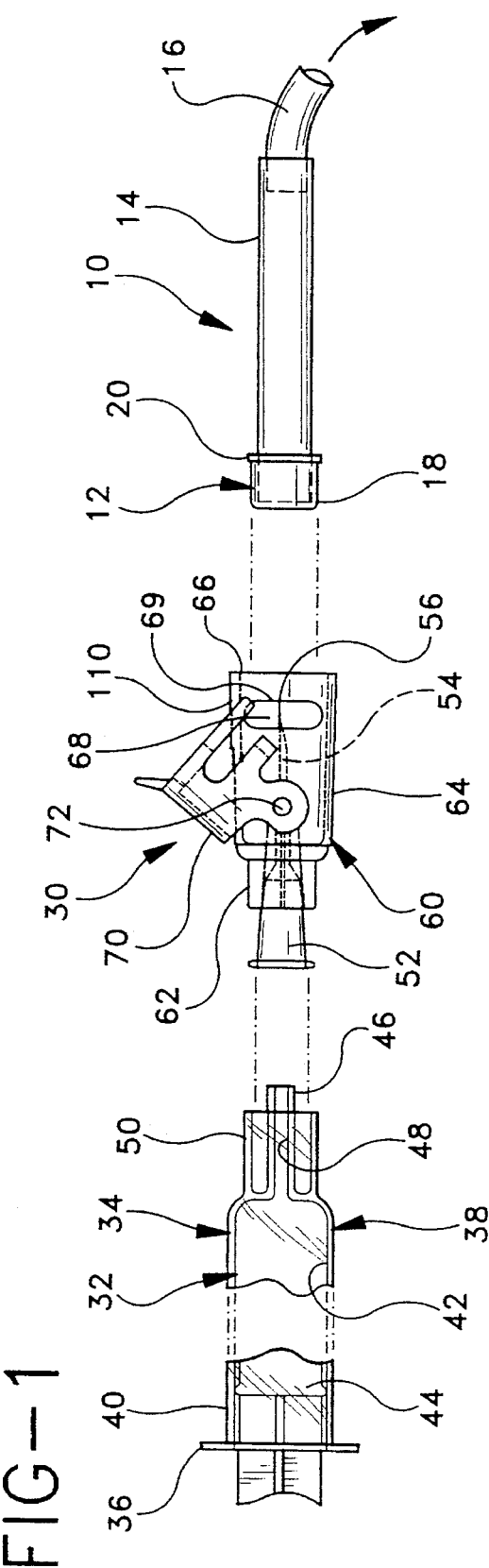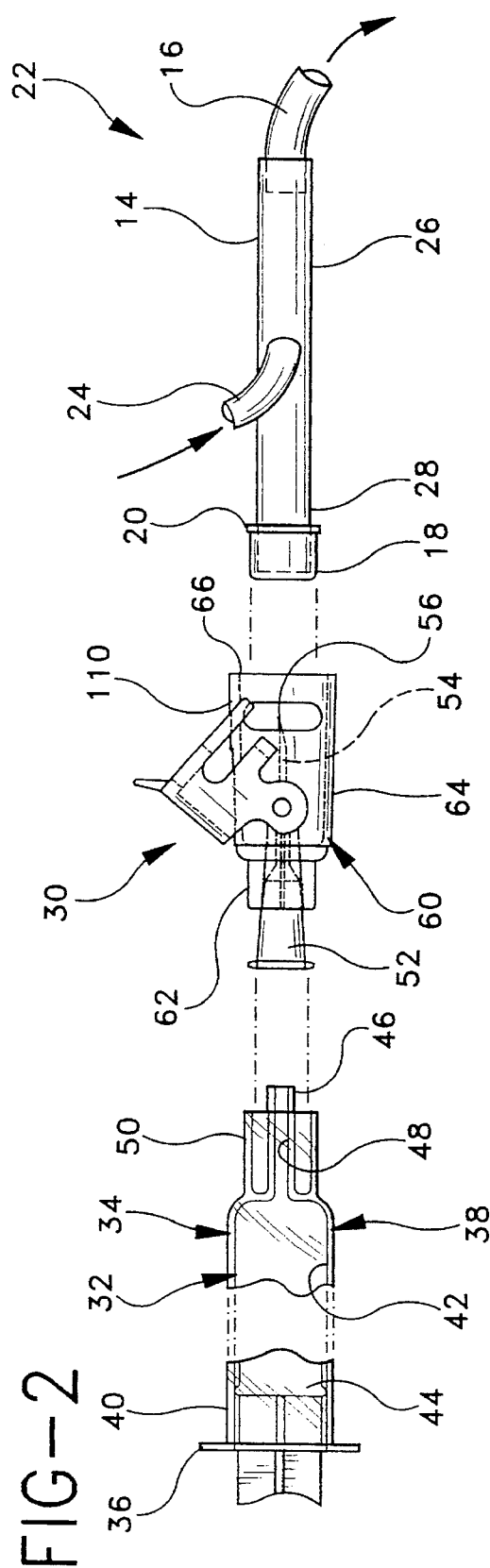

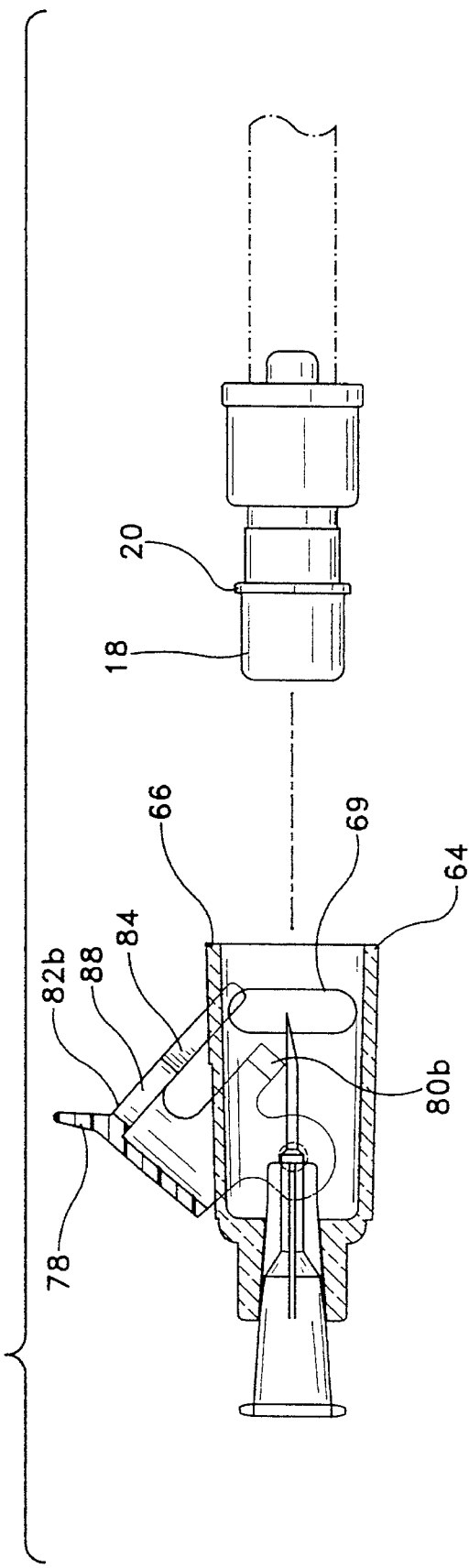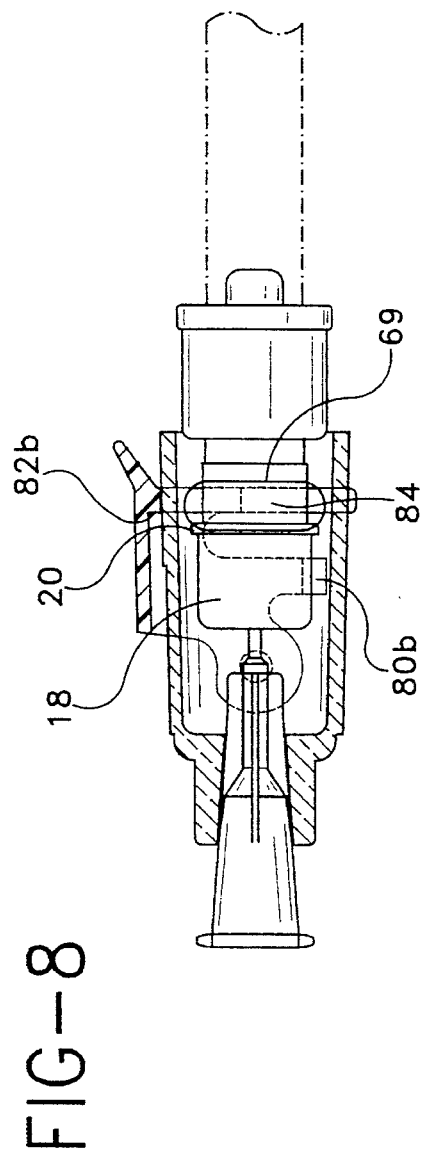

LOCKING SAFETY NEEDLE ASSEMBLY

I. CROSS-REFERENCE TO RELATED APPLICATIONS

This application is a continuation-in-part of Applicants' prior application Ser. No. 07/979,959, filed Nov. 23, 1992, now abandoned.

II. FIELD OF THE INVENTION

The subject invention relates to a safety needle assembly that can be safely, easily and securely locked in communication with a fitting of an intravenous administration set.

III. BACKGROUND

Intravenous ("IV") sets are widely used in the prior art to provide intravenous fluid communication with a patient. The prior art intravenous set includes a needle cannula for insertion into a vein of the patient. The needle cannula communicates with one end of a flexible plastic tube, while the opposed end of the tube is connectable to a flexible bag or bottle containing a fluid to be administered to the patient.

A prior art intravenous set may also include a fitting to which a hypodermic syringe may be used for administering parenteral drugs to a patient. One example of such a fitting is known as a "straight-site." As depicted in FIG. 1, a straight site 10 is a relatively straight fitting, typically made from a plastic material, and includes an injection inlet 12 carrying medication from a source and an outlet portion 14 affixed to a tube 16 which delivers the parenteral drug to the patient. The injection inlet 12 usually includes a diaphragm portion 18, typically made of a rubber or similar compound, which can be pierced by the needle cannula of the syringe carrying the parenteral drug. The diaphragm portion 18, normally configured to be fitted in a fluid-tight manner to the injection inlet, typically defines a lip portion 20 which protrudes from the surface of the injection inlet along the outer circumference of the injection inlet.

A second example of an IV fitting is known in the art as a "Y-site." Referring to FIG. 2, a Y-site 22 is typically a Y-shaped plastic fitting having an inlet leg 24, an outlet leg 26, and an injection leg 28. Like the straight site fitting, the injection leg 28 of the Y-site 22 is also covered by a diaphragm 18 defining a lip portion 20. The diaphragm 18 can be pierced by the needle cannula of a syringe carrying the parenteral drug. The injection leg 28 and the outlet leg 26 of the prior art Y-site typically are collinear with one another, while the inlet leg 24 typically is aligned at approximately 30°–45° to the injection leg.

In use, a needle cannula of a hypodermic syringe carrying the parenteral drug to be administered is pierced through the membrane or septum 18 of the injection inlet of the straight site (FIG. 1) or injection leg of the Y-site (FIG. 2). The hypodermic syringe is used in the standard manner to inject a selected dose of the parenteral drug into the injection leg. The drug is then transported to the patient by the fluid flowing from the injection inlet (or leg) and through the outlet portion (or leg) and toward the patient. A hypodermic needle is often used for introducing medication through the septum. For purposes of illustration but not of limitation, as herein described the medication delivery is implemented through the septum using a syringe. However, it will be understood that the delivery is not so limited and that many fluid delivery devices can be used to provide fluid to the needle which pierces or passes through the septum.

As will be appreciated, the potential for accidental needle sticks is further reduced by prior art needle cannulas having a rigid generally cylindrical shield mounted concentrically around the needle cannula. The shield defines a diameter large enough to telescope over an injection inlet or leg on the intravenous set as the needle cannula enters the fitting. Some such shields are provided with at least one axial extending opening for receiving the inlet leg of a Y-site as remaining portions of the shield are telescoped over the injection leg. A protective shield of this general type is shown, for example, in U.S. Pat. No. Re. 33,617.

Although prior art protective shields, as described above, can reduce the probability of accidental needle sticks, the open end of the axially extending openings still offer a potential for contact with the needle cannula. The potential exists for accidental needlesticks caused by exposed needle cannula. The nurse or other medical personnel utilizing the shield must manually manipulate same to secure the shield to the injection inlet, oftentimes connecting the shield to the inlet with tape. Additionally, a source of intravenous fluid intended for connection to the intravenous fitting can be accidentally disengaged either before its initial use or between successive uses, thereby creating the potential both for contamination of the needle cannula and/or loss of medication, which can potentially be fatal to the patient.

IV. SUMMARY OF THE INVENTION

The subject invention is directed to a safety needle assembly for helping to prevent contamination of a needle cannula or accidental needle sticks and for lockingly retaining a needle cannula to a fitting of an intravenous set. The safety needle assembly includes a rigid needle shield adapted to be disposed around a piercing element, such as a pointed or sharpened needle cannula or a blunt ended needle cannula, to be injected into a fitting of an intravenous set.

The needle shield may include a proximal end for connection to a needle hub which may permanently be affixed to the shield. The needle hub can be removably connected to a syringe barrel or other delivery device, such as an intravenous set. Distal portions of the shield are dimensioned to protectively surround the piercing element. An opening is formed at the distal end of the shield to permit telescopic entry of the fitting into the shield.

The locking safety needle assembly may further include a latch for securely but releasably locking the needle cannula and needle shield to a straight site or appropriately configured Y-site fitting of an intravenous set. The latch may be movable relative to the needle shield between a first position, where the needle shield and needle cannula may be mounted to or removed from the fitting, and a second position, where the needle shield and needle cannula are securely locked on the fitting.

The latch of the subject safety needle assembly may include a pivot arm hingedly mounted to the needle shield for rotation about an axis orthogonal to the needle cannula. The arm can feature two or more pairs of fingers disposed or otherwise formed to surround a portion of the needle shield. One pair of locking fingers may be disposed to selectively engage an outer surface of the shield. These fingers are preferably dimensioned to expand about the housing shield during engagement so as to provide frictional or otherwise positive locking engagement between the latch and the shield. As the latch is disengaged, the fingers slide along the surface of the housing and contract to their original dimension so as to bias the latch away from the shield. These fingers also maintain the latch, when not engaged, in a stable, open position conveniently and readily discernible by the user. Thus, the latch is stable in both the locked and unlocked positions.

A second pair of fingers may be oriented to engage the fitting disposed within the shield and to otherwise constrict the opening at the distal end of the shield so as to prevent inadvertent or accidental separation of the fitting from the shield. These fingers may feature a pair of surfaces which cover a portion of the distal opening, either by unimpeded passage beyond the distal end of the needle shield, or by projecting through openings such as slots cut or otherwise formed through the needle shield. The surfaces engage the lip portion adjacent the injection inlet of the fitting to prevent inadvertent withdrawal of the fitting from the shield. The surfaces may further define a central slot between the fingers which can center the fitting in the shield. The central slot serves to lessen play of the fitting within the shield and to provide additional security against inadvertent detachment of the fitting from the shield. Upon engagement of the latch, the surfaces, either by directly blocking off the distal end of the shield, or by entering into the interior of the shield through the slots, both constrict the distal opening of the sheath and block the lip portion of the fitting, thereby preventing accidental withdrawal of the fitting from the shield.

Preferably, the locking fingers are dimensioned to provide audible and tactile indication of both locking and unlocking of the latch. Thus, the latch is clearly and distinctly movable between either of two extreme positions for selectively locking the safety needle assembly to a fitting or permitting relative mounting or dismounting therefrom.

The tactile and audible locking indication combined with the biasing means provides redundant indication of the locking or unlocking of the safety needle assembly to a fitting. Thus, a health care worker can be positively assured that the needle shield and the needle cannula are positively locked to a fitting, and accidental separation therefrom is positively prevented.

BRIEF DESCRIPTION OF THE DRAWINGS

FIG. 1 is an exploded elevational view of the locking safety assembly in accordance with the subject invention in combination with a hypodermic syringe and a straight-site fitting for an intravenous set;

FIG. 2 is an exploded elevational view of the locking safety assembly in accordance with the subject invention in combination with a hypodermic syringe and a Y-site fitting for an intravenous set;

FIG. 7 is a cross-sectional view of the safety needle assembly prior to engagement with the fitting;

FIG. 8 is a cross-sectional view of the safety needle assembly of FIG. 7 after engagement with the fitting and illustrating retention of the fitting within the shield;

DETAILED DESCRIPTION OF THE PREFERRED EMBODIMENT

Figure 5:
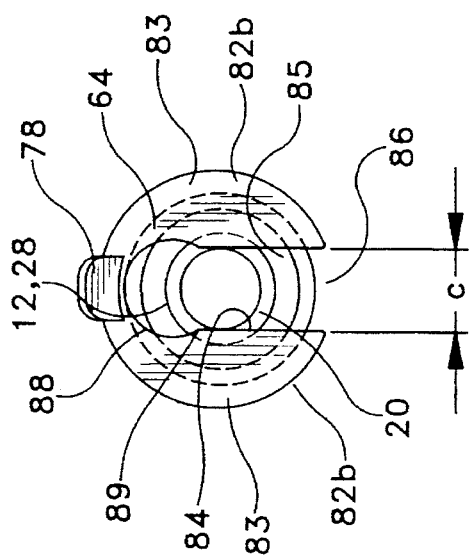
FIG. 5 is a top elevational view of the latch as viewed from the fight side of FIG. 1.
Figure 6:
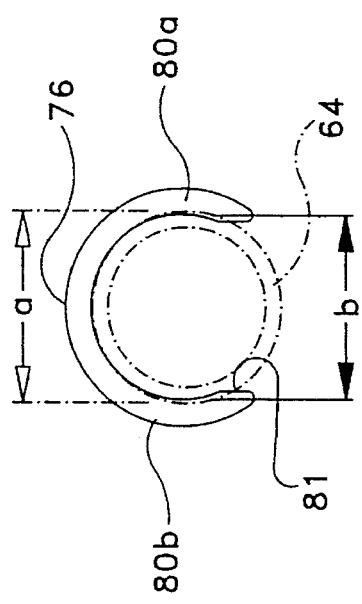
FIG. 6 is a bottom elevational view of the latch as viewed from the left side of FIG. 1.
Figure 3:
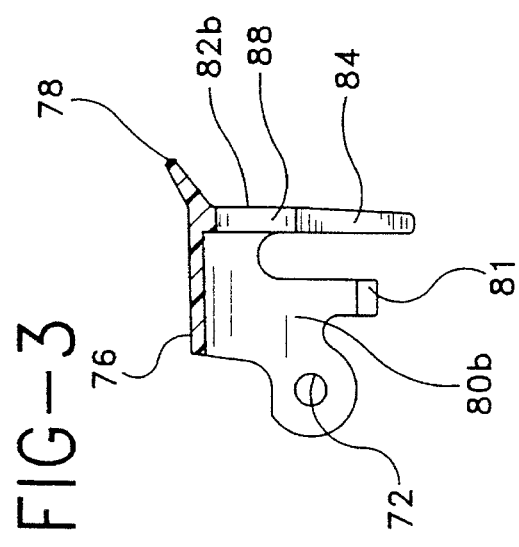
FIG. 3 is a side cross-sectional plan view of the latch of the safety needle assembly.
Figure 4:
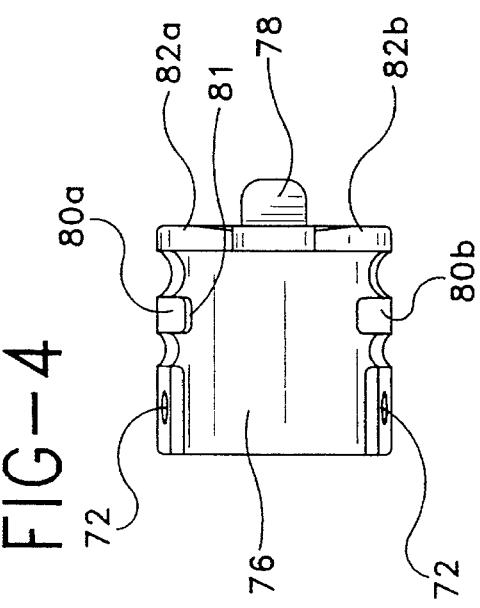
FIG. 4 is a bottom elevational view of the latch.

Turning now to the drawings, wherein like numerals depict like components, a lockable safety needle assembly in accordance with the subject invention is identified generally by the numeral 30 in FIGS. 1 and 2. The safety needle assembly 30 is intended for use with a medical delivery vehicle, such as a hypodermic syringe 32, for delivery of a parenteral drug through an intravenous set having, for instance, a straight site fitting 10 (FIG. 1) or Y-site fitting (FIG. 2). Thus, the locking safety needle assembly is adapted to engage the injection inlet 12 of a straight-site fitting (FIG. 1). Alternately, the assembly may be employed to secure the injection portion 28 of an appropriately configured Y-site fitting (FIG. 2) in a manner to be explained herein. For ease of reference and explanation, operation of the device will be explained principally in reference to the straight-site fitting 10 depicted in FIG. 1. However, it will be understood by those skilled in the art that the invention is not so limited and, as will be seen, the safety needle assembly is readily applicable and can be utilized with an appropriately configured Y-site fitting 22 (FIG. 2).

Referring to FIGS. 1 and 2, hypodermic syringe 32, or another fluid delivery device such as a piggyback intravenous set, can be used with lockable safety needle assembly 30. Syringe 32 includes a generally cylindrical syringe barrel 34 having an open proximal end 36, a distal end 38 and a cylindrical wall 40 extending therebetween defining a fluid receiving chamber 42 within the syringe barrel. A plunger 44 is slidably movable in fluid-tight engagement within the cylindrical wall of syringe barrel 34 for urging fluid in the chamber toward distal end 38. The distal end of syringe barrel 34 includes a tip 46 having a passage 48 extending therethrough and communicating with chamber 42. A generally cylindrical collar 50 is unitarily formed on the distal end of syringe barrel 34 in spaced concentric relationship about the tip 46. The inner surface of collar 50 is provided with an array of internal threads for threadedly receiving the hub of a needle assembly, as explained herein.

As earlier explained, the straight-site fitting 10 (FIG. 1) includes an injection inlet 12 and an outlet portion 14 affixed to a tube 16 for delivery of parenteral medication to a patient. On the Y-site 22 (FIG. 2), an inlet leg 24 is further provided which extends to the Y-site 22 from a supply of fluid (not shown) to be delivered intravenously to a patient.

In either of the fittings described in FIGS. 1 and 2, the injection inlet 12/injection leg portion 28 is intended for use as a port for delivering a parenteral medication to a patient. A diaphragm portion 18, such as a pre-slit septum or pierceable septum, is provided for sealing the injection inlet 12 of the straight-site fitting (FIG. 1) or the injection leg 28 of the Y-site fitting (FIG. 2). The pierceable septum 18 is penetrable by a needle cannula to enable selective communication of a parenteral medication through the injection inlet 12/injection leg 28 and into the stream of fluid being delivered intravenously to the patient. In the case of a pre-slit septum the distal end of the needle cannula can be blunt or unsharpened because it will not be necessary for the needle to pierce the septum but just to pass through the slit. A pre-slit septum and blunt cannula are described in U.S. Pat. No. 4,790,829.

The lockable safety needle assembly 30 of the subject invention may include a needle hub 52 having a piercing element 54 securely connected thereto. Piercing element 54 includes distal end 56 which can be sharpened, as in the case of a sharpened and/or pointed needle cannula, or blunt, depending on the type of septum on the Y-site. For ease of explanation but not of limitation, the device will be principally explained in context with a sharply pointed piercing element 54 such as a needle. The needle hub 52 is threadedly engageable with the collar 50 at the distal end of syringe barrel 34. Thus, threaded connection of hub 52 to collar 50 enables fluid communication from chamber 42 through passage 48 and through needle cannula 54.

Referring to FIGS. 1–8, the lockable safety needle assembly further includes a rigid needle shield 60 having, for instance, a generally tubular base 62 securely and permanently mounted over a distal region of needle hub 52. The shield 60 may include a rigid generally cylindrical sheath 64 projecting distally and about from the base 62 of shield 60 a distance sufficient to protectively surround needle cannula 54. In order to maximize safety against inadvertent contact, it is preferable that sheath 64 completely surround and fully enclose the needle 54, inclusive of the distal end 56. However, it will be fully understood and appreciated by those skilled in the art that the sheath need not extend completely circumferentially around the base 62, nor need the sheath extend lengthwise completely to or beyond the distal end 56 of the needle 54, so long as the sheath at least partially envelop the needle cannula 54 so as to prevent inadvertent touch contact by a user. Thus, the sheath 64 may project, for example, less than 360 degrees around the base of the shield 60, to an extent that the sheath 64 will prevent inadvertent touch contact by a user with the needle 54.

As previously described, the piercing element 54 can be formed in a variety of manners, and principally either as a sharpened needle cannula or as a blunt needle cannula. If formed as a blunt needle cannula, it will be understood that the risk of inadvertent needlestick injury is drastically reduced. Thus, here, the sheath 54 may not extend beyond the distal end 56 of the needle cannula. The blunt needle cannula 54 would be configured to penetrate a pre-slit septum 18.

Figure 9:
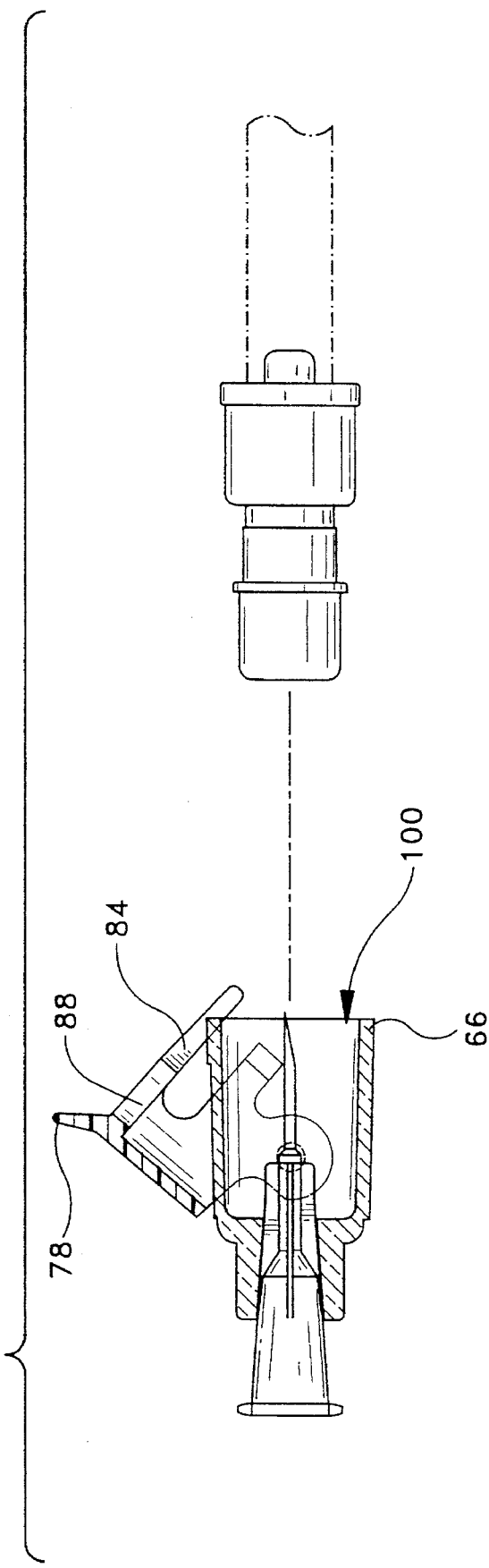
FIG. 9 depicts a cross-sectional view of an alternate arrangement of the safety needle assembly shown prior to engagement with the fitting.
Figure 10:
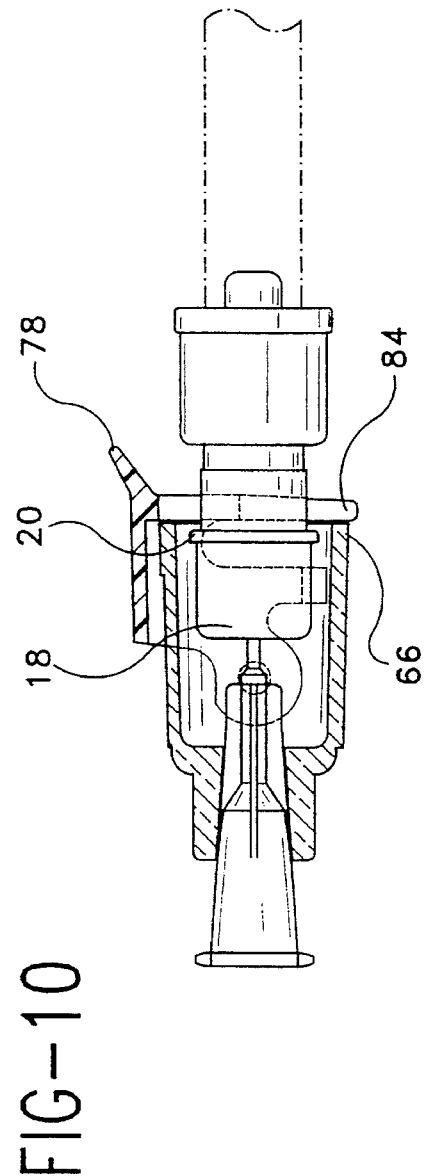
FIG. 10 illustrates the safety needle assembly of FIG. 9 shown after engagement with the fitting and depicting retention of the fitting within the shield.
Figure 12:
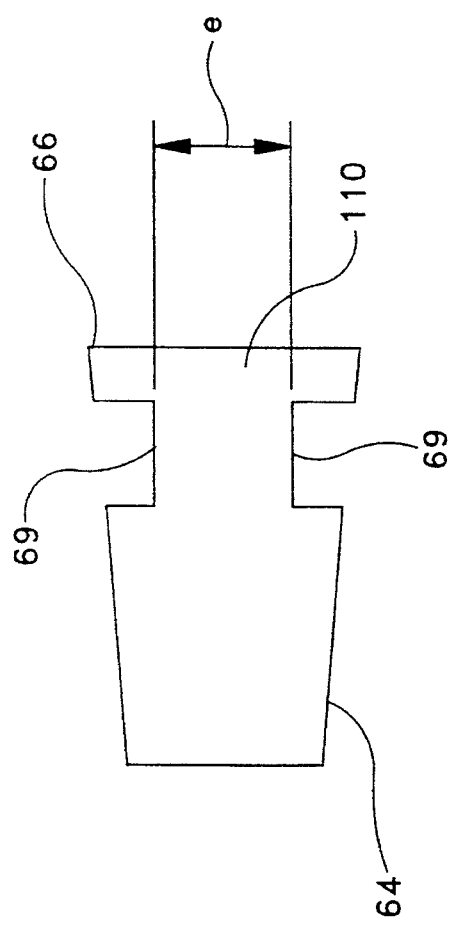
FIG. 12 is a partial top view of the shield depicting the passageways and spine defined along the circumference of the sheath.

The sheath 64 features a distal end 66 that defines a passageway 68 for purposes to be explained herein. As depicted in FIGS. 1–2, 7–8, the passageway 68 may be configured as a pair of opposed slit-like openings 69 extending across the central axis of the shield 60 and around a portion of the circumference of the shield. However, as will be more fully explained and as seen in FIGS. 9–10, it will be also appreciated that the passageway 68 may include a clearance portion 100 disposed at the distal end 66 of the sheath 64. As depicted in FIGS. 1 and 2, and as better seen in FIG. 12, the openings 69 define a spline portion 110 on the outer circumference of shield 60. The spine portion 110 includes a width "e" measured along the outer circumference of the sheath 64.

Figure 11:
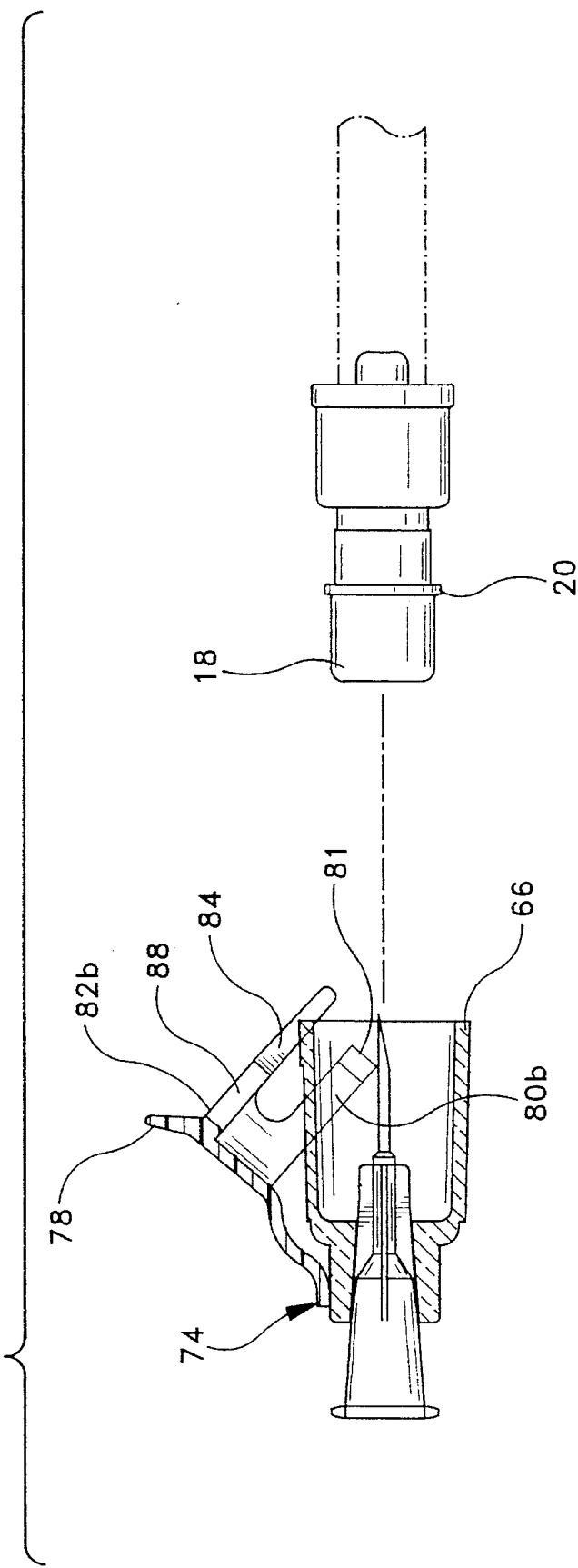
FIG. 11 illustrates the safety needle assembly depicting the latch affixed to the shield via a living hinge arrangement.

Lockable safety needle assembly 30 further includes a latch 70 hingedly connected, for instance, to shield 60 at a pivot location 72 intermediate the passageway 68 and base 62. Latch 70 is hingedly mounted for rotation about an axis orthogonal to needle cannula 54 and lying in or parallel to a plane passing centrally through the longitudinal midpoints 69a of the openings 69. As will be realized by those skilled in the art, in lieu of a pivot connection 72, a plastic living hinge 74 (FIG. 11) may connect the latch 70 and the shield 60 for allowing pivoted rotation of the latch with respect to the shield.

Latch 70, as best seen in FIGS. 3–6, includes a pivot arm 76 which extends generally distally from pivot point 72 and terminates in an actuating projection 78 which is dimensioned and configured to enable the pivoting movement to be generated easily by a thumb or a forefinger. Latch 70 further features means for securing the latch 70 with the shield and means for securing the fitting within the shield. As here illustrated, for purposes of illustration but not of limitation, two pairs of finger members 80a, b, and 82a, b projecting out from the pivot arm 76 in a circumferential manner, are provided to secure the latch to the shield, and to secure the fitting within the shield, respectively. Each of the pairs of finger members 80 a, b and 82 a, b can be molded integrally with the latch 70. It will however be understood and realized by those skilled in the art that both means may be configured in various manners. For instance, a single finger member 80 and a single finger member 82 may be provided in lieu of respective pairs to serve the same purpose or, as will be further described herein, a one-piece multi-function configuration (FIGS. 13–15) may be employed in lieu of separate finger members 80, 82. Other variants within the ambit of the skilled artisan are possible.

As shown, finger members 80 a, b are disposed intermediate fingers 82 a, b and pivot 72. The latch 70 is preferably formed of a thermoplastic or similar material so that fingers 80 a, b are resiliently expandable and contractible at their juncture with pivot arm 76 in a manner to hinge about pivot arm 76. For purposes to soon to be explained, finger members 80a, b are configured to define an inner diameter "a" (FIG. 6) which, in a contracted, non-expanded state, is slightly less than the outer diameter "b" of the sheath 64. The fingers 80 a, b further include respective ramping portions 81, here depicted as planes generally orthogonal to the axis of pivot arm 76. As will be further explained, the ramping portions smooth the transition of fingers 80 a,b about the sheath 64 as the latch is engaged (or disengaged), thereby assisting the expansion (or contraction) of the fingers 80 a,b about the sheath 64.

Referring again to FIGS. 3–6, second finger members 82 a, b are located at or adjacent a distal end of latch 70. The fingers 82 a, b each include a respective planar flange portion 83. These flange portions 83 may feature respective opposed edge portions 84 substantially orthogonal to the axis of pivot arm 76. For purposes to be explained, and as seen in FIG. 5, the opposed edge portions 84 are disposed on the flanges 83 so as to define between them a slot-like opening 86 having a width "c" preferably substantially equal to the diameter of the outside surface of injection inlet 12/injection leg 28. The spine portion 110 on the sheath 64 can be formed to a width "e" slightly wider than the width "c" defined by the opposed edge portions 84. A rounded opening; 88 is also formed between the flanges 83 adjacent both the actuating projection 78 and an innermost end 89 of the slot 86. As will be appreciated, the rounded opening 88 is formed somewhat wider than the slot 86 and may be configured dimensionally to accommodate the width "e" of spine portion 110 created by the portion of the sheath 64 circumference disposed between the opposed slit-like openings 69.

Operation of the locking safety assembly is relatively straightforward and will now be generally explained referring to FIGS. 1, 3–8. Lockable safety needle assembly 30 can be used by initially connecting the needle hub 48 to collar 32 at distal end 20 of hypodermic syringe 12. Lockable satiety needle assembly 10 may then be employed with a straight site 10 intravenous set by inserting the injection inlet 12 into the sheath 64. Sheath 64 is then telescoped over the straight site sufficiently for the sharp distal end 56 of needle cannula 54 to pierce and pass through pierceable septum 18 on injection inlet 12(see. eg, FIGS. 7 and 8). As previously mentioned, if the straight site includes a pre-split septum, the distal end of the needle may be blunt, rather than sharp. As seen in FIG. 8, when straight site 10 is completely seated in the sheath 64, the entire septum 18 is contained within the interior of sheath 64, with the lip portion 20 positioned proximally of the passageway 68.

After full seating of sheath 64 on the injection inlet of straight site 10, latch 70 is rotated about pivot point 72 and toward sheath 64. Rotation of pivot arm 76 toward sheath 64 first urges ramping portion 81 of the finger members 80a, b into sliding engagement with the outside surface of shield 60. Ramping forces cause sufficient hinging deflection of the fingers 80a, b about pivot arm 76 to enable further rotation of pivot arm 76 toward sheath 60. Continued rotation of pivot arm 76 causes the finger members 80a, b to continue to expand and hinge outward from the pivot arm 76, so that fingers 80a,b frictionally, positively embrace the shield 60. Because the inner diameter "a" between finger members 80a, b is slightly less than the outer diameter "b" of the sheath 64, there will be exerted a positive biasing or gripping action by finger members 80a, b towards and around the sheath 64 to stably retain the latch 70 in a locked condition (FIG. 8).

The deflection and subsequent locked engagement of locking fingers 80a, b with sheath 64 can be configured to provide a distinct audible and/or tactile indication of the locked condition of latch 70 relative to sheath 64. Similarly, the deflection and subsequent resilient return of latch 70 in response to opening forces exerted on the latch may also generate a distinct audible and tactile indication of the opened condition. Furthermore, as seen in FIG. 1, because the inner diameter "a" between the finger members 80a, b is slightly less than the outer diameter "b" of the sheath, the finger members 80a, b are prevented from passing around the sheath 64 absent the exertion of force by a user. Thus, the finger members 80 a,b will conveniently position and retain the latch 70 in a stable, open position readily discernible by the user, with the inlet of the ramping members 81 engaging the outer surface of the sheath 64. Thus, the finger members 80 a, b provide a dual, bi-stable function for the latch: They serve both to stably return latch 70 in a closed condition when engaged with the shield 70, and they serve to stably secure the latch 70 open against the shield 62 when the latch is not locked with the shield.

As the latch arm 76 is rotated into locked position with the sheath 64, the second pair of finger members 82a, b are likewise urged to retain the straight-site 10 within the shield 60. Rotation of finger members 82a, b causes the flanges 83 to approach the surface of sheath 64. Rather than strike the outside surface of the sheath, the flanges will pass through the passageway 68 (FIG. 8). When the latch is fully engaged (see FIGS. 5 and 8), the flanges 83 will serve to constrict the distal opening 85 defined by the interior of the sheath 64, thus aiding to prevent inadvertent touch contact with the end 56 of the needle 54. Simultaneously, it will be seen that upon engagement of the latch 70, the lip portion 20 of the straight site 10 is captured in the interior of the sheath 64 by the flanges 83. Because the width of the slot 86 is less than the width of the lip 20, the lip 20 will be prevented from inadvertent withdrawal from the sheath 64 so as to secure straight site 10 to shield 60. As can also be observed, the slot 86 between opposed edge portions 84 of the flanges may be configured so as to enable the edge portions to engage the exterior surface of injection inlet 12 (injection leg 28), thus lending further stability to the connection between the needle safety assembly and the fitting, and to otherwise center the injection inlet (leg) with the interior of the sheath 64.

Added security against inadvertent opening of the latch 70 is provided by the rounded opening 88 formed on the latch. When the latch is in its engaged position, the rounded opening 88 will "capture" therein the spine portion 110 of the shield 60 so as to provide added security against inadvertent opening of the latch. It will be recalled that the width "c" defined between the opposed edge portions 84 can be configured slightly smaller than the width "e" defined by the spine portion 110. As the finger members 82a, b can be molded of the same resilient material as fingers 80a, b, during engagement the finger members 82a, b will likewise hinge at their intersection with latch arm 76 so as to pass about spine portion 110. When the innermost end 89 of the slot 86 passes the spine portion, the flanges will contract to their original orientation, causing spine portion 110 to be caught in opening 88.

FIGS. 9 and 10 depict a variant of the embodiment previously described. As in the previous embodiment, the safety needle assembly 30 also features a rigid needle shield 60, inclusive of a generally cylindrical sheath 64 projecting distally from the base of the shield. A latch 70, inclusive of two sets of finger members 80a, b and 82 a,b as previously described, is also provided. As here illustrated, the distal end of needle 56 is shown slightly projecting from the sheath 64. However, as previously explained, it will be appreciated that the length of the sheath 64 and its circumferential extension about the base of the shield 60 may be chosen by the skilled artisan, as need or desire dictate, in order to ensure that the needle cannula 54 be encapsulated to an extent to prevent inadvertent touch contact by the user.

In this embodiment, the finger members 82a, b do not pass through a passageway which is formed through the surface of the shield; rather, the relative dimensions of the sheath 64, latch arm 76 and finger members 82a,b are chosen so that the flanges 83 pass through a passageway defined by a clearance portion 100 disposed adjacent the distal end 66 of the sheath 64. As illustrated in FIG. 10, in this configuration, the flanges 83 will come to rest against the distal end 66 of the sheath 64 rather than disposed in the interior of the sheath. As in the previous embodiment, the flanges 83 will constrict the distal opening 85 of the sheath, thus minimizing the potential for touch contact with the needle cannula. In addition, as before, the septum 18 will be fully captured within the interior of the sheath 64, with the lip portion 20 engaged by the proximal surface of the flanges 83 so as to retain the fitting within the shield. The opposed edge portions 84 of the flanges serve also to center and engage the injection inlet 12 of the fitting.

As before, the finger members 80a, b will grippingly, securely engage the latch with the shield 60 so as to prevent inadvertent opening of the latch 70. Furthermore, additional security may be provided by the frictional engagement produced between opposed edge portions 84 and the exterior surface of the inlet 12. While not here illustrated, if desired, the spine portion 110 previously described may be provided as an extension jutting from the distal end 66 of the sheath 64. The spine portion will be retained by the opening 88 of the latch 70 to provide extra security against inadvertent disengagement by the latch.

As previously noted, the safety needle assembly 30 of the invention is equally amenable to use with either a straight-site fitting 10 as depicted in FIG. 1 or with an appropriately configured Y-site fitting 22 as shown in FIG. 2. Unlike the straight site fitting, the injection leg 24 of the Y-site fitting may potentially interfere with the componentry associated with the locking needle assembly 30. It will be realized, however, that the dimensions of the sheath 64, latch arm 76 and/or length of the injection inlet 28 can be chosen, as need or desire dictate, so that the inlet leg 24 is spaced away from either the finger members 82a, b and/or the sheath distal end 66 so as to avoid interference between them. For instance, the sheath 64 and/or latch arm 76 may be shortened so as to avoid hitting the inlet leg 24. Similarly, the injection inlet 28 can be lengthened so as to space the inlet leg 24 away from the distal end of the sheath or from interfering with the flanges 83. By providing unimpeded access to the injection leg 28, complete enclosure of the septum 18 and lip portion 20 within the interior of the shield 60 is assured, and secure engagement of the needle assembly with the fitting is accomplished.

Figure 13:
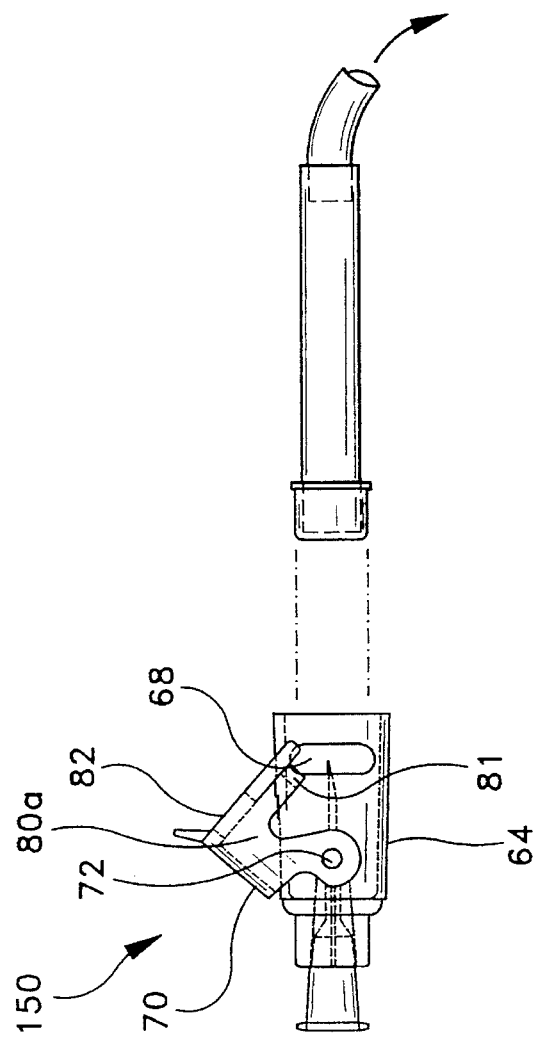
FIGS. 13–15 illustrate a one-piece multi-functional configuration for forming the finger members.
Figure 15:
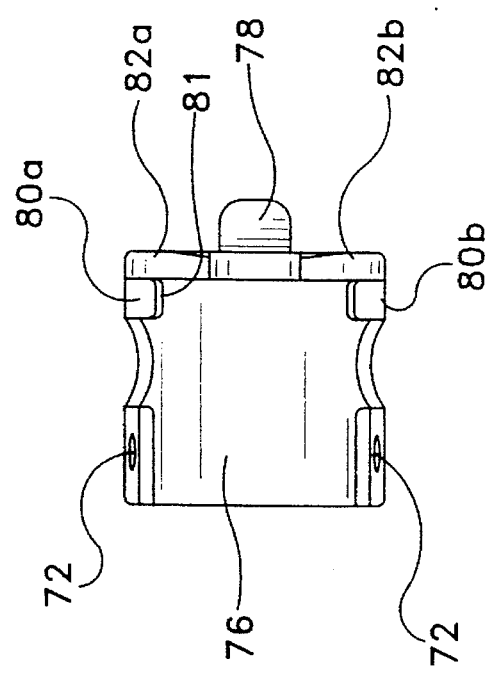
Figure 14:
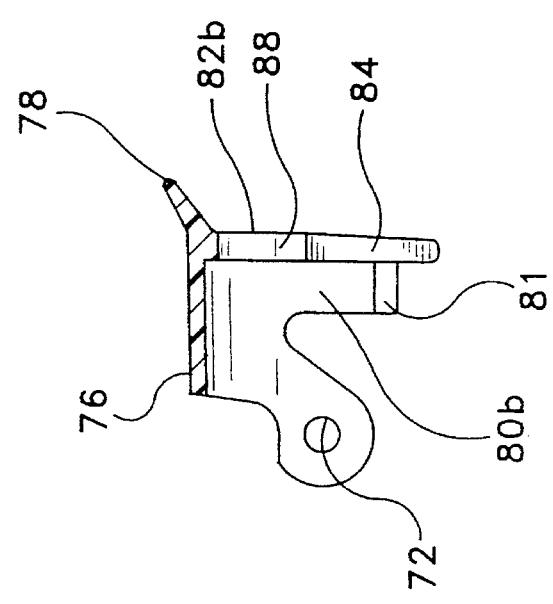

Modifications of the structure of finger members 80 a, b and 82 a, b are possible. For instance, as best illustrated in FIGS. 13–15, rather than provide a distinct pair of finger members 80 a, b intermediate the pivot point 72 and the pair of second finger members 82 a,b, a pair of one-piece multifunctional configurations 150 may be formed to provide the features associated with the first finger members 80a, b and the second finger members 82a, b. As earlier explained, the configurations 150 may be integrally molded with the latch. Also, in lieu of a pair, a single configuration 150 may be provided to serve the same purpose. The function of this embodiment is substantially identical to those previously described. As illustrated, the second finger member 82a (or 82b) portion of the configuration 150 is disposed through passageway 68, with the first finger member 80a (or 80b) portion of the configuration disposed for engagement with a portion of sheath 64. As before, in lieu of passageway 68, the second finger member portion 82a (b) may also pass through a clearance portion 100 disposed adjacent the distal end 66 of the sheath 64. Here, the dimensions of the various components may be chosen so as to ensure that the finger member portion 80a (b) of the configuration 150 will not overshoot the distal end of the shield 60 so as to engage some potion of the shield 60.

It will be appreciated by those skilled in the art that additional and further forms of the invention may be realized without departing from the spirit and scope of the appended claims, it being understood that the invention is not limited to the specific embodiments shown.

What is claimed is:

1. A safety needle assembly for secure connection of a piercing element to an intravenous fitting, comprising:

a protective shield defining a base portion, the shield disposed around said piercing element and including a sheath portion projecting from and about the base a sufficient distance to at least partially envelop the piercing element, the sheath having a distal end defining a passage dimensioned to receive at least a portion of said intravenous fitting therein; and a latch pivotable about said protective shield for releasably engaging the intravenous fitting within the shield, said latch comprising a pivot arm having an end pivotably connected to the protective shield, means for releasably engaging a portion of the shield spaced a distance from said pivotable end, and means for releasably locking a portion of said intravenous fitting in said shield, said means for releasably locking spaced a second distance from said pivotable end.

2. The safety needle assembly as recited in claim 1, wherein said means for releasably locking a portion of the intravenous fitting comprises at least one flange member for preventing inadvertent withdrawal of said intravenous fitting from said protective shield, 3. The safety needle assembly as claimed in claim 2, wherein said at least one flange member is selectively engageable against a lip portion of said intravenous fitting to prevent inadvertent withdrawal of the fitting from said protective shield.

4. The safety needle assembly as recited in claim 1, wherein the sheath defines a passage for accommodating said means for releasably locking a portion of the intravenous fitting.

5. The safety needle assembly as recited in claim 4, wherein said passage comprises an opening formed in the sheath.

6. The safety needle assembly as recited in claim 1, wherein said means for releasably engaging the protective shield comprises at least one resilient finger member adapted to be biasingly disposed around at least a portion of the shield.

7. The safety needle assembly as recited in claim 6, wherein said finger member is configured to stably maintain said latch in an open position against said shield.

8. The safety needle assembly as recited in claim 6, wherein said finger member comprises a ramping portion for facilitating biasing engagement of said finger member with said at least a portion of the shield.

9. The safety needle assembly as recited in claim 1, wherein the pivot arm is pivotably connected to said protective shield via a living hinge.

10. The safety needle assembly as claimed in claim 1, wherein said latch is pivotable about an axis parallel to a plane aligned with a plane defined by the passage at the distal end of the sheath.

11. The safety needle assembly as claimed in claim 1, wherein said latch is pivotable about an axis substantially orthogonal to a plane aligned with a plane defined by the passage at the distal end of the sheath.

12. A safety needle assembly for secure mounting to an injection site of an intravenous set, the injection site including an injection portion, an outlet portion, comprising:

a cannula assembly including a needle hub for mounting to a fluid delivery vehicle and a piercing element projecting distally from the hub;

a protective shield defining a base portion mounted onto the needle hub, said shield defining a sheath portion projecting from and about the base a distance to at least partially envelop the piercing element, the sheath having a distal end defining a passage dimensioned to receive the injection portion of said injection site; and a latch pivotable about said protective shield for releasably locking the injection site within the shield, the latch comprising a pivot arm having an end pivotably connected to the protective shield, at least one shield locking member spaced at least a distance from the pivot for releasably engaging the latch with a portion of the shield, and at least one member spaced a second distance from said pivot for releasably engaging said injection portion.

13. The safety needle assembly of claim 12, wherein said piercing element is a sharp needle cannula.

14. The safety needle assembly of claim 12, wherein said piercing element is a blunt cannula.

15. The safety needle assembly as claimed in claim 12, wherein said injection site comprises a straight site.

16. The safety needle assembly as claimed in claim 12, wherein said injection site comprises a Y-site.

17. The safety needle assembly of claim 12, wherein said shield locking member is configured to maintain said latch in a stable open position against said shield and to retain said latch in a stable closed position when engaged with said shield.

18. The safety needle assembly of claim 17, wherein an audible or tactile indication is produced when said latch is engaged with said shield.

19. The safety needle assembly according to claim 12, wherein said shield locking member comprises a resilient finger element defining a radius less than a radius defined by said at least a portion of the sheath, wherein said finger element is resiliently biased about said at least a portion of the sheath as said latch is engaged by a user.

20. The safety needle assembly according to claim 19, wherein said finger element further comprises a ramping portion for urging said finger element about said sheath as said latch is engaged by a user.

21. The safety needle assembly according to claim 12, wherein said member for releasably engaging the injection portion includes a flange member for blocking inadvertent withdrawal of the injection portion from the shield.

22. The safety needle assembly of claim 21, wherein said injection portion of the injection site includes a lip portion formed wider than the injection portion, said flange member blocking withdrawal of the lip portion to capture the lip portion within the sheath.

23. The safety needle assembly of claim 12, wherein said sheath defines a passageway, said at least one member for releasably engaging said injection portion passing through said passageway.

24. The safety needle assembly of claim 12, wherein said latch arm is pivotably affixed to said shield via a living hinge.

25. The safety needle assembly of claim 12, wherein said at least one member for releasably engaging the shield provides an audible indication of locking engagement with said shield.

26. A safety needle assembly for secure mounting to a straight-site of an intravenous fitting, the straight-site including an injection portion and an outlet portion, comprising:

a cannula assembly including a needle hub for mounting to a fluid delivery vehicle and a needle cannula projecting distally from the hub;

a protective shield defining a base portion mounted onto the needle hub, said shield defining a generally cylindrical sheath portion projecting from and about the base a distance to at least partially envelop the needle cannula, said sheath having a distal end defining a passage within the shield dimensioned to receive the injection portion of said straight site; and a latch pivotable about said protective shield for releasably locking the straight site within the shield, the latch comprising a pivot arm having an end pivotably connected to the protective shield, said latch further comprising at least one finger member spaced a distance from the pivot for releasably engaging the latch with a portion of the shield and at least one site engaging member spaced a second distance from the pivot for releasably engaging the straight site within the shield, said site engaging member including a flange portion disposed through a passageway defined by said sheath for lockingly engaging a lip portion of the straight site so as to prevent inadvertent withdrawal of the straight site from the shield.

27. A safety needle assembly for secure connection of a piercing element to an intravenous fitting, comprising:

a protective shield defining a base portion, the shield disposed around said piercing element and including a sheath portion projecting from and about the base a sufficient distance to at least partially envelop the piercing element, the sheath having a distal end defining a passage dimensioned to receive at least a portion of said intravenous fitting therein; and a latch pivotable about said protective shield for releasably engaging the intravenous fitting within the shield, said latch comprising a pivot arm having an end pivotably connected to the protective shield and at least one multifunctional member for releasably engaging a portion of the shield and for releasably locking a portion of said intravenous fitting in the shield, said member spaced a distance from said pivotable end.

28. The safety needle assembly of claim 27, wherein said multifunctional member comprises:

a first portion for releasably engaging a portion of said shield; and a second portion for releasably locking a portion of said intravenous fitting in the shield.

29. A safety needle assembly for connection to an intravenous fitting, comprising:

a piercing element securable to said intravenous fitting;

a protective shield defining a base portion, the shield for disposition around said piercing element and including a sheath portion projecting from and about the base a sufficient distance to at least partially envelop the piercing element, the sheath having a distal end defining a passage dimensioned to receive at least a portion of said intravenous fitting therein; and a latch pivotable about said protective shield for releasably engaging the intravenous fitting within the shield, said latch comprising a pivot arm having an end pivotably connected to the protective shield, means for releasably engaging a portion of the shield spaced a distance from said pivotable end, and means for releasably locking a portion of said intravenous fitting in said shield, said means for releasably locking spaced a second distance from said pivotable end.

30. The safety needle assembly of claim 29, wherein said piercing element is a pointed needle cannula.

31. The safety needle assembly of claim 29, wherein said piercing element is a blunt cannula.

* * * * *